(12) United States Patent
Valmikinathan et al.

(10) Patent No.: US 11,992,579 B2
(45) Date of Patent: May 28, 2024

(54) POROUS FOAMS DERIVED FROM EXTRACELLULAR MATRIX, POROUS FOAM ECM MEDICAL DEVICES, AND METHODS OF USE AND MAKING THEREOF

(71) Applicant: ACell, Inc., Columbia, MD (US)

(72) Inventors: Chandra M. Valmikinathan, Secaucus, NJ (US); Nikhil Niraj Gheewala, Bethesda, MD (US); Brent Donald Young, Centennial, CO (US); Thomas Wayne Gilbert, Ellicott City, MD (US)

(73) Assignee: ACell, Inc., Columbia, MD (US)

( * ) Notice: Subject to any disclaimer, the term of this patent is extended or adjusted under 35 U.S.C. 154(b) by 110 days.

(21) Appl. No.: 17/105,780

(22) Filed: Nov. 27, 2020

(65) Prior Publication Data

US 2021/0077661 A1    Mar. 18, 2021

Related U.S. Application Data

(63) Continuation of application No. 14/860,781, filed on Sep. 22, 2015, now abandoned.

(60) Provisional application No. 62/055,056, filed on Sep. 25, 2014.

(51) Int. Cl.
| | | |
|---|---|---|
| *A61L 27/36* | (2006.01) | |
| *A61L 27/56* | (2006.01) | |
| *B33Y 70/00* | (2020.01) | |
| *B33Y 10/00* | (2015.01) | |
| *B33Y 80/00* | (2015.01) | |

(52) U.S. Cl.
CPC ....... *A61L 27/3633* (2013.01); *A61L 27/3691* (2013.01); *A61L 27/56* (2013.01); *B33Y 70/00* (2014.12); *B33Y 10/00* (2014.12); *B33Y 80/00* (2014.12)

(58) Field of Classification Search
None
See application file for complete search history.

(56) References Cited

U.S. PATENT DOCUMENTS

| | | | |
|---|---|---|---|
| 4,902,508 A | 2/1990 | Badylak et al. | |
| 4,956,178 A | 9/1990 | Badylak et al. | |
| 5,554,389 A | 9/1996 | Badylak et al. | |
| 6,099,567 A | 8/2000 | Badylak et al. | |
| 6,379,710 B1 | 4/2002 | Badylak | |
| 6,576,265 B1 | 6/2003 | Spievack | |
| 8,025,896 B2 * | 9/2011 | Malaviya | A61L 27/56 |
| | | | 424/422 |
| 8,802,436 B1 | 8/2014 | Kentner et al. | |
| 9,119,831 B2 | 9/2015 | Kentner et al. | |
| 9,238,091 B2 | 1/2016 | Kentner et al. | |
| 2004/0166169 A1 | 8/2004 | Malaviya et al. | |
| 2007/0248638 A1 * | 10/2007 | Van Dyke | A61K 35/34 |
| | | | 424/422 |
| 2008/0260831 A1 | 10/2008 | Badylak et al. | |
| 2011/0237552 A1 | 9/2011 | Heinemann et al. | |
| 2014/0219963 A1 | 8/2014 | Badylak et al. | |
| 2014/0227364 A1 | 8/2014 | Kentner et al. | |
| 2014/0271472 A1 * | 9/2014 | Patel | A61L 24/0005 |
| | | | 424/1.85 |

FOREIGN PATENT DOCUMENTS

| | | | | |
|---|---|---|---|---|
| CN | 101801428 A | 8/2010 | | |
| CN | 103611193 A | 3/2014 | | |
| JP | 2008-194968 A | 8/2008 | | |
| WO | 1996015818 A1 | 5/1996 | | |
| WO | 2013/181375 A1 | 12/2013 | | |
| WO | 2014/039427 A1 | 3/2014 | | |
| WO | 2014039429 A1 | 3/2014 | | |
| WO | WO-2014039429 A1 * | 3/2014 | ............. | A61K 35/12 |
| WO | 2014/124203 A1 | 8/2014 | | |

OTHER PUBLICATIONS

Office Action dated Mar. 12, 2020 in Chinese Application No. 201580051825.9, 9 pages.
English Translation of Office Action dated Aug. 8, 2019 in Chinese Application No. 201580051825.9.
Office Action dated Aug. 8, 2019 in Chinese Application No. 201580051825.9.
European Office Action for Application No. 15 778 810.0, dated Feb. 4, 2019.
Japanese Office Action dated Nov. 12, 2018 for Japanese Patent Application No. 2017-515699, English translation included (8 pages).
Canadian Patent Office, Canadian Office Action, Canadian Patent Application No. 2,962,203, dated Apr. 23, 2018, 5 pages.
Japanese Office Action, Japanese Patent Office, Japanese Patent Application No. 2017-515699, dated Mar. 19, 2018, 9 pages.
International Preliminary Report and Written Opinion in corresponding PCT Application No. PCT/US2015/051328 dated Apr. 6, 2017. (9 Pages).
Patent Cooperation Treaty, International Search Report (ISR) & Written Opinion of the ISR, International Application No. PCT/US2015/051328, dated Dec. 7, 2015; 14 pages.
Freytes et al., "Preparation and rheological characterization of a gel form of the porcine urinary bladder matrix," Biomaterials 29(11):1630-1637, 2008.

* cited by examiner

*Primary Examiner* — H. Sarah Park
(74) *Attorney, Agent, or Firm* — Eva Tan

(57) ABSTRACT

The invention disclosed herein is directed to a porous wound healing foam composition that is made from an extracellular matrix of a mammal, method of making, and method of using.

8 Claims, 6 Drawing Sheets

POROUS FOAMS DERIVED FROM EXTRACELLULAR MATRIX, POROUS FOAM ECM MEDICAL DEVICES, AND METHODS OF USE AND MAKING THEREOF

RELATED APPLICATION

This application a continuation of U.S. patent application Ser. No. 14/860,781, filed on Sep. 22, 2015, which claims priority to and benefit of U.S. provisional application 62/055,056 filed Sep. 25, 2014, which are incorporated by reference herein in their entireties for all purposes.

FIELD OF THE INVENTION

The invention described herein is directed to tissue restoration porous foams derived from extracellular matrix material of mammalian tissues, medical devices made therefrom, methods of use, and methods of making thereof.

BACKGROUND

Materials useful for restoring wounds derived from the extracellular matrix (ECM) of mammalian tissues have been described in numerous publications including but not limited to ECMs described in U.S. Pat. Nos. 6,576,265, 4,902,508, 4,956,178, 5,554,389, and, 6,379,710 each of which is incorporated by reference herein in their entirety for all purposes. ECMs include but are not limited to small intestine submucosa (SIS), urinary bladder submucosa (UBS), urinary bladder matrix (UBM; includes epithelial basement membrane), dermis (PD), and liver basement membrane (LBM). ECMs useful for restoring wounds as wound healing materials are typically applied as a sheet, a gel, a powder or a particulate of various sizes, a liquid, or as a three dimensional non-sheet like shape.

A disadvantage of forms of ECM derived wound healing materials in the prior art is their relative two-dimensional (planar) nature. Other prior art wound healing materials are sheets, powders, or gels that are challenging to use in void-filling applications, for example, voids in trauma-induced wounds, and are challenging to use as hemostats. Furthermore, flowable ECM scaffolds useful for direct-to-wound delivery or coating of other synthetic polymer scaffolds often require enzymatic degradation of the ECM scaffold for their production of the flowable ECM scaffold. Enzymatic degradation is undesirable because it is desirable to remove the enzyme from medical materials that are introduced into a human. Removal of the enzyme in medical materials is technically challenging.

Accordingly, new ECM compositions with improved flowability, improved coating properties, improved formability to three-dimensional constructs for applications such as void filling, improved ease of use from multiple applications to a wound to less frequent applications, e.g., a single application to a wound, and accelerated healing are needed in the field of regenerative medicine. Additionally, new ECM compositions with improved flexibility and coating properties can be addressed from preparation techniques that would provide additional advantages from a manufacturability perspective, e.g., elimination of enzymatic degradation. Additionally, new ECM compositions should be more resistant to separation from its carrier, e.g., saline, than compositions described in prior art. Known ECM compositions tend to settle out from the carrier within hours, whereas the current ECM composition remains in suspension for extended periods of time, e.g., greater than 1 week. The invention described below is advantageous over known ECM wound compositions because it solves the problems described above of known ECMs.

SUMMARY OF THE INVENTION

The foregoing and other objects, features and advantages of the invention will become apparent from the following more particular description of the preferred embodiments of the invention.

In one aspect, the invention is directed to a method for making a medical foam device. In one embodiment, the method begins with an extracellular matrix material such as UBM, LBM, UBS, SIS or others, dehydrating the ECM, followed by solubilizing the dehydrated ECM in a solution comprising, for example, a pH less than 4.0 or a pH greater than 9.0. The solubilized ECM is blended, for example, in an industrial blender at speeds of 500-2500 RPM to form a foamy extracellular matrix slurry. The foamy ECM slurry is next neutralized in solution by the addition of acid or base as required to about pH 7 and mixed. In one embodiment, the foamy ECM slurry may be used as the "ink" in a three-dimensional printer for making a three-dimensional medical device, coated on a three dimensional object such as a surgical implant and dehydrated. Alternatively, the ECM slurry may be added to a mold followed by dehydrating the molded slurry to make a medical device.

The dehydrated slurry may also be particularized and used for medical applications. A medical gel may be made from the dehydrated particularized slurry by mixing the dehydrated particularized slurry in a solution.

In another aspect, the invention is directed to a medical device manufactured from ECMs as described above. The device may be a mineralized device including one or more of the following materials: calcium, phosphate, calcium and phosphate salts, calcium nitrate, calcium hydroxide, calcium carbonate, calcium oxide, sodium phosphate, sodium dehydrogen phosphate, phosphoric acid, demineralized or decellularized bone matrix, powdered allogenic bone, hydroxyapatite and tricalcium phosphates.

The medical device of the invention may be a gel, a sheet-form or a three-dimensional form shaped to mimic an anatomical structure, or shaped to fill a void, as non-limiting examples, or otherwise configured for implantation at a site of injury. The medical device comprises at least the dehydrated foamy extracellular matrix material having pore sizes in the range of 1 micron to 500 microns, 100 micron to 250 microns, or 100-150 microns, for example.

In one embodiment of the invention, the medical device is molded. In an alternative embodiment, the medical device is 3-D printed (printed from a three-dimensional printing printer).

In yet another embodiment, the medical device of the invention is a conventional medical device that is coated with the foamy extracellular matrix slurry material. The medical device may take on a variety of shapes depending on the tissue void to be filled, the tissue needing augmentation, the size and shape of the injured tissue, and porosity, such as sponge-like, needed for the particular application, to name but a few applications and shapes. Additionally, the foamy extracellular matrix material has anti-inflammatory, analgesic, and anti-microbial properties.

In another embodiment of the invention, the dehydrated extracellular matrix slurry material may be particularized and added to a solution such as water, saline, or other physiological buffers to form a gel, a tissue glue, or other solubilized forms of the ECM made from an ECM slurry according to the invention described herein.

BRIEF DESCRIPTION OF THE FIGURES

The invention is described with particularity in the appended claims. The further advantages of the invention described herein may be better understood by referring to the following description taken in conjunction with the accompanying drawings.

DESCRIPTION OF THE INVENTION

Compared to prior art wound healing ECM derived materials, the porous ECM-derived foams according to the invention described below have at least the following advantages:
(1) the use of a sheet-like architecture as a starting material to generate a three dimensional porous architecture for a medical device;
(2) controlled pore size of foams derived from ECM;
(3) mineralized ECM foams with selectable porosity;
(4) enhanced ability to stay in a suspension sufficiently long to generate flowable matrices;
(5) enhanced coatability of medical devices with a flowable slurry of ECM foam;
(6) preparation of three-dimensional shapes, for example, shapes of a medical device, non-limiting examples such as pins, wraps, tubes or other hollow structures, splints, valves, staples, sponges, bone implants, or meshes;
(7) enhanced capacity to promote rapid endogenous wound healing;
(8) anti-inflammatory, analgesic, and anti-microbial properties;
(9) non-enzymatic degradation;
(10) single application of the disclosed porous ECM foam promotes faster healing than single application of prior art ECM wound healing products;
(11) enhanced flowability;
(12) printable (3-D printing);
(13) moldable.

Figure 1:
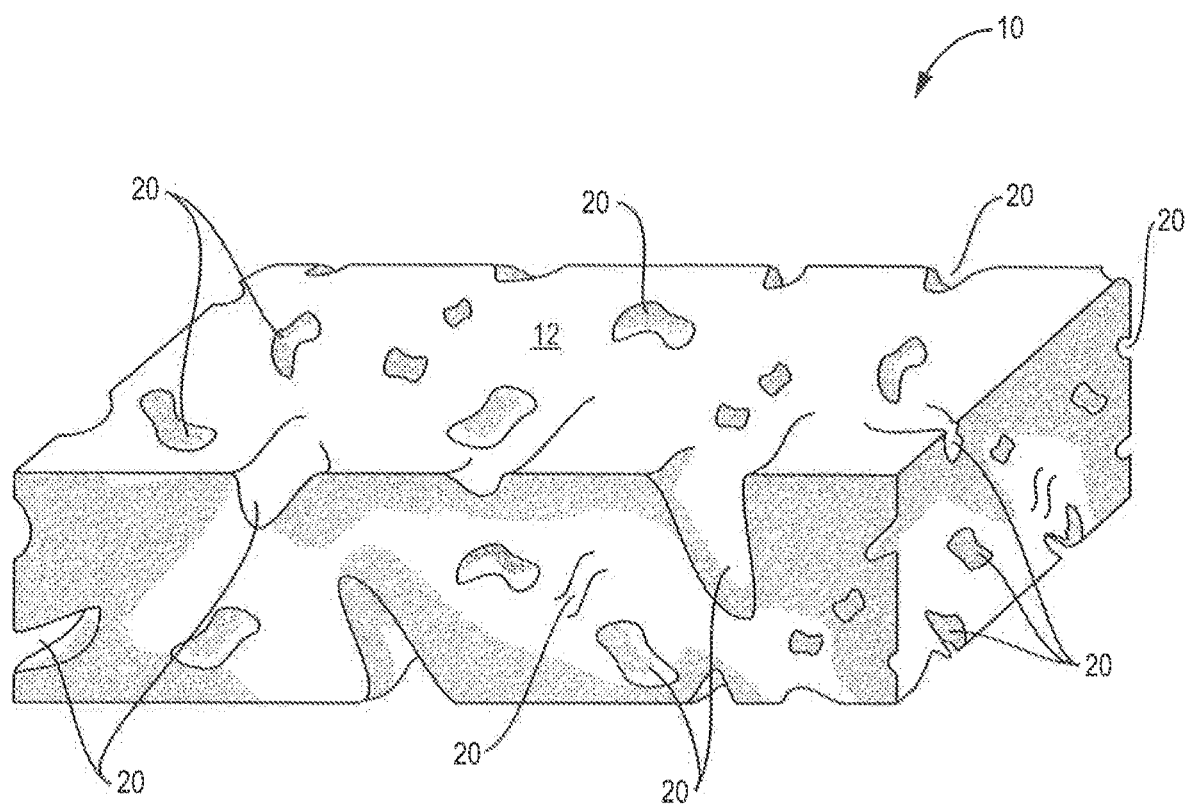
FIG. 1 illustrates a porous cuboidal ECM foam according to one embodiment of the invention.

In one aspect, referring to FIG. 1, the invention relates to a wound healing material 10 comprising an extracellular matrix (ECM) but not limited to SIS, UBS, UBM and LBM, for example, that is processed to form a porous ECM foam. A foam is defined as porous, if the majority of the volume in the three dimensional foam comprises cavities (pores) 20 that are empty or capable of being filled with a gas such as air or a fluid. These cavities may be filled with, for example, body fluids, such as blood, or other solutions such as a growth factor cocktail, vascular endothelial growth factor, nerve growth factor, fibroblast growth factor, epidermal growth factor, or saline. The porous ECM foam may be partially or entirely solidified by lyophilization or air-drying to form a sheet, i.e., a planar shape, or other three dimensional (i.e., non-planar) medical device. The porous ECM foam may be shaped to form any shape including but not limited to cuboidal ECM foams for surgical staple thickness compensation and reinforcement, porous bone implants and sponges, porous tube shapes for applications as a nerve graft or arterial prosthesis, or porous sheets of various thickness as porous wound healing matrices and porous dermal repair scaffolds, and specifically shaped materials for filling tissue defects and/or for tissue augmentation after tissue resection or plastic surgery.

Referring to FIG. 1, the size of the pores 20 in the interior of the porous ECM foam 10, according to the invention, may differ from the size of the pores 20 that appear on the exterior of the porous ECM foam. The internal diameter of the pores range from about 1 micron to 500 microns, about 100 microns to 250 microns, and more particularly, about 100-150 microns, for example. Pore sizes in this range are ideal for cell infiltration and exchange of body fluids or cell culture media and the nutrients associated with those fluids.

In a particular embodiment of the invention, porous foams are mineralized by the addition of, for example, calcium salts or phosphate salts, calcium nitrate, calcium hydroxide, calcium carbonate, calcium oxide and other calcium salts or phosphate salts from sodium phosphate, sodium dihydrogen phosphate and phosphoric acid, and combinations thereof. Mineralized foams are applicable to repair of boney orthopedic injuries, such as filling gaps in a patient's bone fracture which otherwise would require harvesting bone from another site in the patient to fill the gap, spinal injuries, or head (skull) injuries.

In another embodiment of the porous ECM foam according to the invention, the solidified porous ECM foam is milled to produce a fine porous ECM particulate or powder. Such powdered porous ECM foams, for example, may be aspirated into a syringe for injection as a wound healing composition at the site of tissue injury in a patient. The size of the particulate in particulate porous ECM foams varies, for example, from about 1 nm to 1 millimeter, more particularly from 1 micron to 1 millimeter. Specifically, particulate size in the range of 100 microns to 500 microns is preferred for flowable mixtures of the particulates. Particulates, upon mixing with appropriate amounts of liquid for infusion, for example, water, saline, or phosphate buffered saline, can produce a flowable mixture such as a gel, for example. As used herein, the term "flowable" means capable of being poured or extruded at room temperature. Typical applications of the porous ECM foam particulate-containing flowable mixtures include but are not limited to wound healing, dermal fillers, bone and spinal applications (especially the mineralized foams), and intra-articular applications including applications for the treatment of arthritis including but not limited to osteoarthritis, rheumatoid arthritis, other inflammatory arthritis types, degenerative arthritis, septic arthritis including but not limited to Lyme disease, gout, and traumatic arthritis.

In another embodiment of the porous ECM foams according to the invention, the porous foams may be applied to a medical device by coating, for example, including but not limited to coating a surgical mesh, suture material, and other planar and substantially three-dimensional medical device structures. As used throughout, the term "medical" means related to the practice of medicine or surgery. Coating may be accomplished by, for example, spraying, dipping, application with a brush or rolling.

In another embodiment of the invention, the porous ECM foam slurry according to the invention may be applied to the lumen of a tube or to otherwise form an ECM rod. The porous ECM foam slurry-filled rod may be used for applications such as regeneration of nerve fibers or fistula closure. In a non-limiting embodiment, the rod may be formed, for example, from a sheet or a multi-layer sheet of an ECM, UBM, for example, or a sheet made from the ECM slurry. The rod is formed by rolling the sheet(s) into a cylindrical shape and filling the tube with the porous ECM foam slurry. Alternatively the porous ECM foam slurry may be spread on the ECM sheet before it is rolled up, and then rolled up into a cylindrical shape enclosing the porous ECM slurry.

For neuro-regeneration applications, for example, one end of a severed nerve may be joined to one end of a ECM rod and the other end of the severed nerve may be joined to the other end of the ECM rod, therefore acting as a guidance channel to promote neurogenesis.

For fistula repair applications, for example, the rod formed by rolling a ECM sheet and foam into a cylinder can be inserted into the fistula. In one embodiment of the invention, the ECM composition could be modified such that after insertion through the fistula tract the rod would swell to fill the irregular geometry upon hydration, for example, with saline.

Figure 2A:
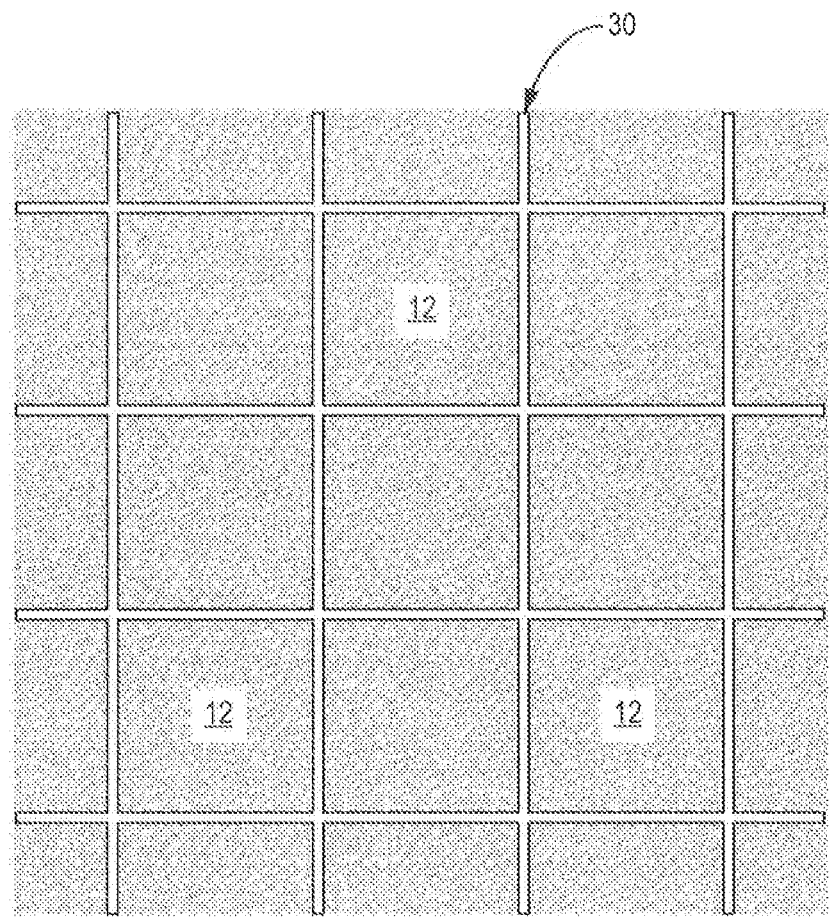
FIGS. 2A-2C illustrate various embodiments of a mesh according to the invention.
Figure 2B:
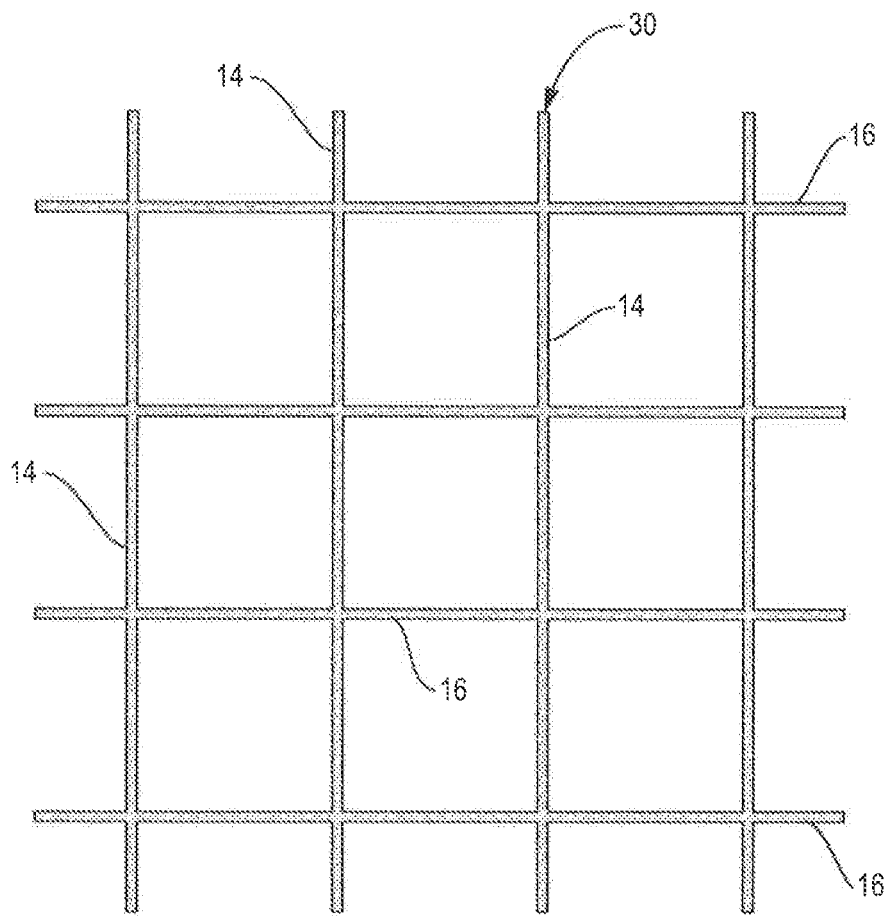
Figure 2C:
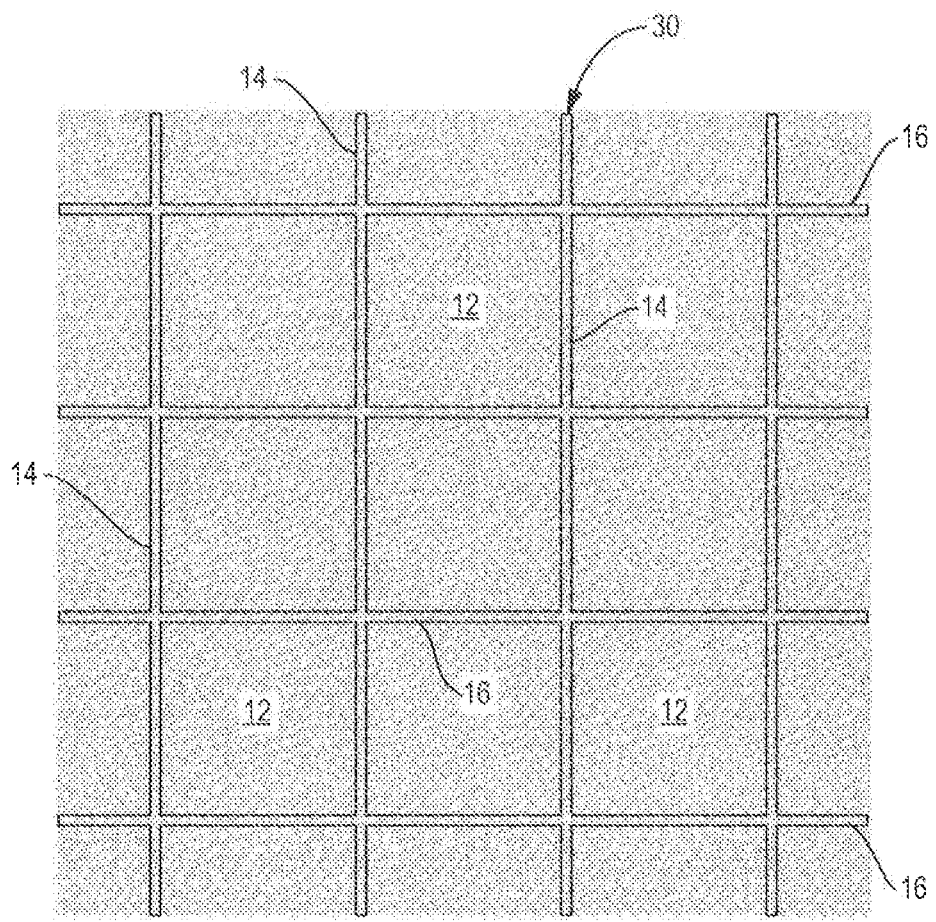

In another embodiment of the invention with respect to a mesh 30, referring to FIG. 2A, the porous ECM foam according to the invention may be embedded within spaces 12 of the mesh 30 as shown in FIG. 2A, applied on the warp and/or weft 14, 16 of the mesh as a coating as shown in FIG. 2B, or both embedded within spaces 12 and coated on the warp 14 and/or weft 16 of the mesh 30 as shown in FIG. 2C. The embedded porous ECM foam mesh may be made, for example, by sandwiching a layer of mesh between two layers of foam slurry, as described above, and lyophilized. The lyophilized foams that are obtained can be vacuum pressed either after hydration in water or saline or without hydration, in a vacuum press to obtain one continuous laminated mesh like construct. By this approach, the ECM on one side of the foam integrates with the ECM on the other side by becoming embedded through the pores of the mesh.

Typical applications for such porous ECM foam enhanced medical devices include but are not limited to hernia repair, application to infected fields, minimization of tissue adhesions to synthetic mesh, breast reconstruction, tissue expanders and/or tissue augmentation, anti-inflammatory or anti-microbial applications, and analgesia.

In yet another embodiment, the porous ECM foam according to the invention, operates as a carrier for bioactive molecules, drugs, and other pharmaceutical agents. For example, porous ECM foams, according to the invention, are applied to tissue voids as defect fillers following tumor resection. Chemotherapeutic drugs may be added to these foams. For example, the porous ECM foams are carriers for growth factors, small molecules and other molecules targeted to the treatment of diseases such as cancer and diabetes, anti-inflammatory drugs such as steroids and non-steroidal anti-inflammatory agents (NSAIDS), anti-microbial agents, and analgesics for pain relief.

In another aspect, the invention is directed to a method for making porous foams derived from ECMs. Sources of ECMs include but are not limited to UBS, UBM, SIS and LBM described above.

In one embodiment of the manufacturing method of the invention, UBM, is prepared as described in U.S. Pat. No. 6,576,265, incorporated by reference herein in its entirety. Briefly, the urinary bladder is removed from a mammal, e.g., pig, sheep, or cow, and the bladder wall is delaminated from the luminal epithelial cells by, for example, but not limited to, soaking the urinary bladder in a hypertonic saline solution for 10 minutes to 120 minutes. Soaking removes the epithelial cells from the underlying epithelial basement membrane. The layers of the epithelial tissue that remain after this initial step are the epithelial basement membrane and all of the layers abluminal to the epithelial basement membrane, i.e., at least the tunica propria, tunica submucosa, tunica muscularis and tunica serosa. One or more tissue layers, for example, tunica propria, tunica muscularis mucosa, tunica submucosa, tunica muscularis and tunica serosa are selectively removed by mechanical abrasion or other mild chemical treatment to form the UBM matrix.

After the one or more abluminal layers are selectively removed from the urinary bladder or other epithelial tissue, the resulting matrix includes the epithelial basement membrane lining the luminal surface of the matrix and from which epithelial cells and substantially all cellular elements are removed, and one or more tissue layers, for example, tunica muscularis mucosa, tunica propria, tunica submucosa, tunica muscularis and tunica serosa abluminal to the epithelial basement membrane.

Figure 3:
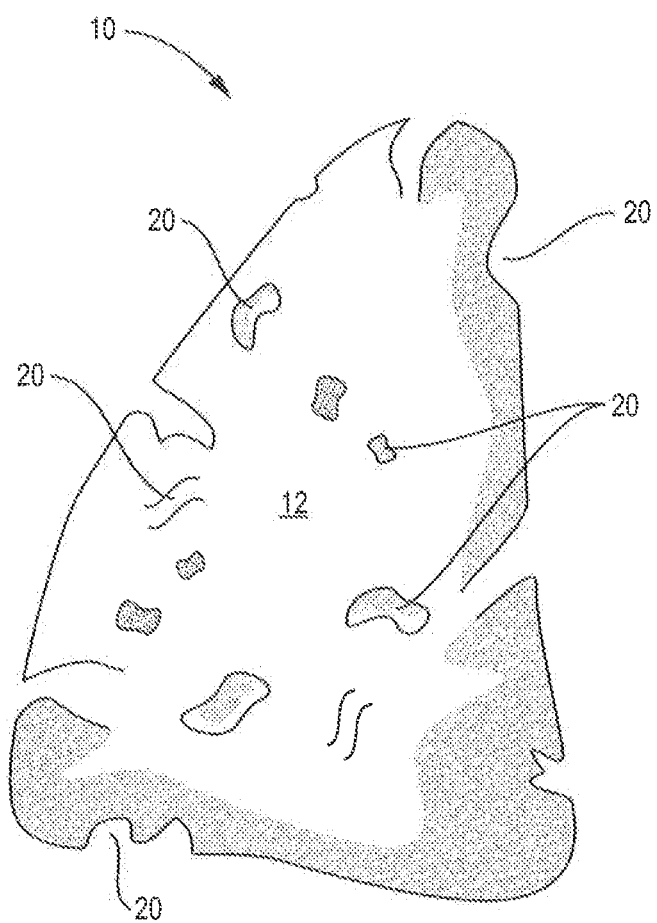
FIG. 3 illustrates a porous ECM foam in the shape of a body part according to one embodiment of the invention.

The ECM, such as UBM described above, is rehydrated in hydrochloric acid or sodium hydroxide at a concentration range from about 1 N to 0.001 N, preferably at 0.1-0.01 N HCl, more preferably at 0.01 N HCl, for approximately 5 minutes and, in a blending step, blended in an industrial blender at speeds of about 500 RPM to 2500 RPM, preferably at 2000 RPM, to produce a foamy flowable ECM slurry. The foam ECM slurry may then be neutralized, at room temperature, in, for example, a base such as NaOH, ranging in concentration from about 0.01N to 1N, preferably between 0.1N and 1N, more preferably at 1N. Other bases such as KCl, or $NaHCO_3$, are also useful for neutralizing the acid used to make the foamy ECM slurry. Once the base, such as NaOH, is added to the acidic foamy ECM slurry, the slurry is again briefly blended to uniformly neutralize the slurry prior to scaffold fabrication. Typically, the foamy ECM slurry is then poured into a mold to form a planar or anatomically shaped three-dimensional porous ECM foam, based on the anticipated wound healing application. For example the three dimensional porous rigid or semi-rigid ECM foam may be shaped as a cylindrical rod, a tube, a cube, or a body part 10, e.g., a nose as shown in FIG. 3, or ear, breast, cardiac valve, dental alveolus, and other complex three-dimensional tissues. As described above, molds for specific device applications include, for example, but are not limited to, cuboidal molds for cuboidal porous ECM foams for stapled surgical staple thickness compensation and reinforcement, for bone implants and sponges, for tube shaped molds to form porous ECM tubes for applications as a nerve graft, venous or arterial prosthesis, tracheal prosthesis, esophageal or intestinal replacement or anastomosis, or sheet molds for forming porous ECM sheets as porous ECM topical wound healing or hernia repair matrices, and/or for porous ECM dermal repair scaffolds.

After the foam ECM slurry is introduced into the mold, the slurry is then lyophilized or air dried under specific conditions, as described below, to produce a molded solid or semi-solid, i.e., not flowable, porous ECM foam device. The pore sizes on the interior of the porous ECM foam device as well as on the exterior of the porous ECM foam device can be controlled by lyophilization temperatures as well as by the materials used as the mold. Using the process described below, pore sizes on the exterior to the interior of the foam device ranging from, for example, 1 micron (04) to 500 microns, 100 microns to 250 microns, or 100-150 microns may be obtained. Pore size may vary based on the concentration of ECM in solution and based on the rate for freezing.

The general lyophilization step of the ECM slurry includes pre-cooling of the lyophilizer shelves to a temperature ranging from 25° C. to −40° C., from 4° C. to −20° C., or specifically from −10° C. to −20° C. Pre-cooling is followed by stabilizing the molded slurry at a temperature ranging from 0° C. to −40° C., from 0° C. to −20° C., specifically from −10° C. to −20° C., for periods of time ranging, for example, from between 0 minutes to 240 minutes, 0 minutes to 120 minutes, or 60 minutes to 120 minutes, to allow for ice crystal formation. During this step, the lyophilizer shelves are cooled at rates of 0.01 C°/min to 1 C°/min, for example or at 0.1 C°/min to 1 C°/min. The ice formed from the ECM slurry during this step is then sublimated by vacuum at the temperatures for stabilizing the molded porous ECM foam slurry described above. The vacuum pressure used is typically in the range of 100-120 mm Hg.

In a particular embodiment of the method of making porous ECM foams, calcium and phosphate salts, ranging from calcium nitrate, calcium hydroxide, calcium carbonate, calcium oxide and other calcium salts and phosphate salts from sodium phosphate, sodium dehydrogen phosphate and phosphoric acid are added to the blending step above to make mineralized porous ECM foams. The ratios of the above salts can be varied by altering the molar ratios, specifically to yield calcium phosphate concentrations known in the art to mimic native bone in vivo. These salts react in-situ to form mineralized three dimensional foams, as described above. The choices of acid (e.g., phosphoric vs hydrochloric), molar ratios of the calcium and the phosphate salts, and pH can lead to changes in the microstructure of the mineral component of the foam, such as brushite, apatite, monetite. Alternatively, the foams can also be fabricated in sodium hydroxide, with the addition of one of the components of the mineral, for example calcium ions or phosphate ions, and lyophilized first and then the alternate salt (phosphate, if calcium is used in the first step) can be included in solution, immediately following lyophilization, to allow for mineralization in the foams. This is then followed by re-lyophilization to obtain mineralized foams.

Furthermore, other sources of mineral, specifically titanium or magnesium derived, or "bone-like" resorbable mineral silicate derived mineral can also be used as alternatives to simple calcium phosphate salts. Also, demineralized or decellularized bone matrix, powdered allogenic bone, hydroxyapatite and tricalcium phosphates can be used as calcium phosphate sources during blending for scaffold preparation.

For example, in order to manufacture one of the above foams with tricalcium phosphate, 0.3 M calcium nitrate is added along with 0.2 molar ammonium sodium phosphate, during the blending process described above. Alternatively other combinations can be achieved by reacting a range of phosphoric acid solutions from 0.01M to 1M, with several sources of calcium, for example, calcium nitrate, calcium acetate, calcium hydroxide, or combinations thereof, with concentration in the range of 0.1M to 1M, for example, 0.1 M to 0.5M. The ratios of calcium nitrate to calcium hydroxide can be tailored from 1:1 to 10:1, depending on the type of mineral to be obtained as mentioned earlier.

In another embodiment, the porous ECM foam devices are milled to produce a fine powder (e.g., less than 250 microns) and loaded into a syringe. The milling process can vary from mortar and pestle, cryo-milling, blade milling to wire milling. The size and the volume of the porous ECM foam particles required will dictate the milling process that is used. The size of the milled particles ranges from about 1 nm to 1 millimeter, particularly from about 1 micron to 1 millimeter. For flowable mixtures of porous ECM particulates, particulate sizes in the range of 10 microns to 500 microns are preferred. To form a solution of particulate porous ECM foams, an appropriate amount of water, saline, or phosphate buffered saline, for example, is used to produce a flowable mixture that does not separate into different phases over a significant period of time (e.g., more than 7 days, 1-7 days, 2-5 days, or 3-4 days,). Typically for 10-1000 mg of porous ECM foam powder, a range of 100 microliters to 1 milliliter saline or other fluid would yield flowable mixtures with varying properties for different applications. Typical applications include wound healing, dermal fillers, fillers for hair transplantation, bone and spinal applications (for mineralized foams), including applications for treatment of osteoarthritis.

In another embodiment of the method, the porous ECM foams described above can be applied to medical devices such as a mesh, sutures, and other planar or three dimensional structures. Such applications on medical devices lead to reduced scarring and enhanced healing. In one embodiment, mesh and similar architectures are embedded within or laid on either side of the ECM foamy slurry prior to lyophilization of the porous ECM foamy slurry. Alternatively, the medical device structure may be dipped into, painted, or sprayed with the ECM foam slurry prior to its lyophilization. In yet another embodiment, the ECM foamy slurry is the "ink" in a 3-D printing process used to manufacture a planar or three-dimensional medical device. Similarly, porous ECM foams may be made into three dimensional meshes. Typical applications for such porous ECM foam meshes include but are not limited to hernia repair, fistula repair, contaminated site application, anti-adhesive applications, breast reconstruction and application of tissue expanders and tissue augmentation.

Exemplification of the Invention

Porous foams were generated as UBM from urinary bladder as described above. Sheets of UBM were soaked in 0.01 M hydrochloric acid for 30 minutes to obtain a uniform ECM slurry. The slurry was poured in a mold and was lyophilized to obtain a uniform porous foam. The lyophilized porous foam was made with a thickness of about 6 mm, and was cut to a diameter of 20 mm using a biopsy punch to form a foam disc. The foam discs were packaged in double-peel Tyvek pouches and terminally-sterilized with electron beam irradiation for evaluation in management of full-thickness wounds in the dorsal skin of three adult pigs.

At least 10 lyophilized foam discs per pig, one foam disc per defect site, were implanted on the skin defect on the dorsal side. The foam discs were implanted dry and then covered with saline moistened gauze to hydrate the foam disc. The saline soak gauze was covered with a non-adherent dressing. Wound dimensions were measured at multiple time points including immediately post-implantation, Day 1, Day 2, Day 12, Day 14, Day 18 and Day 21. Control wounds on the same animal were treated with either saline-moistened gauze, a single application of intact UBM particulate (MicroMatrix®, ACell, Inc.) (1×), or repeated applications of intact UBM particulate on Day 0, Day 4, Day 7, and Day 14 (4×). The wound size was measured using calipers and quantified using images taken with a Aranz Silouette camera. For example, healing was designated as 100% (100% of the wound diameter remained) and 0% (the wound was completely healed leaving no defect). Histology was also performed to evaluate the healing potential and the quality of healing post-foam application.

Figure 4:
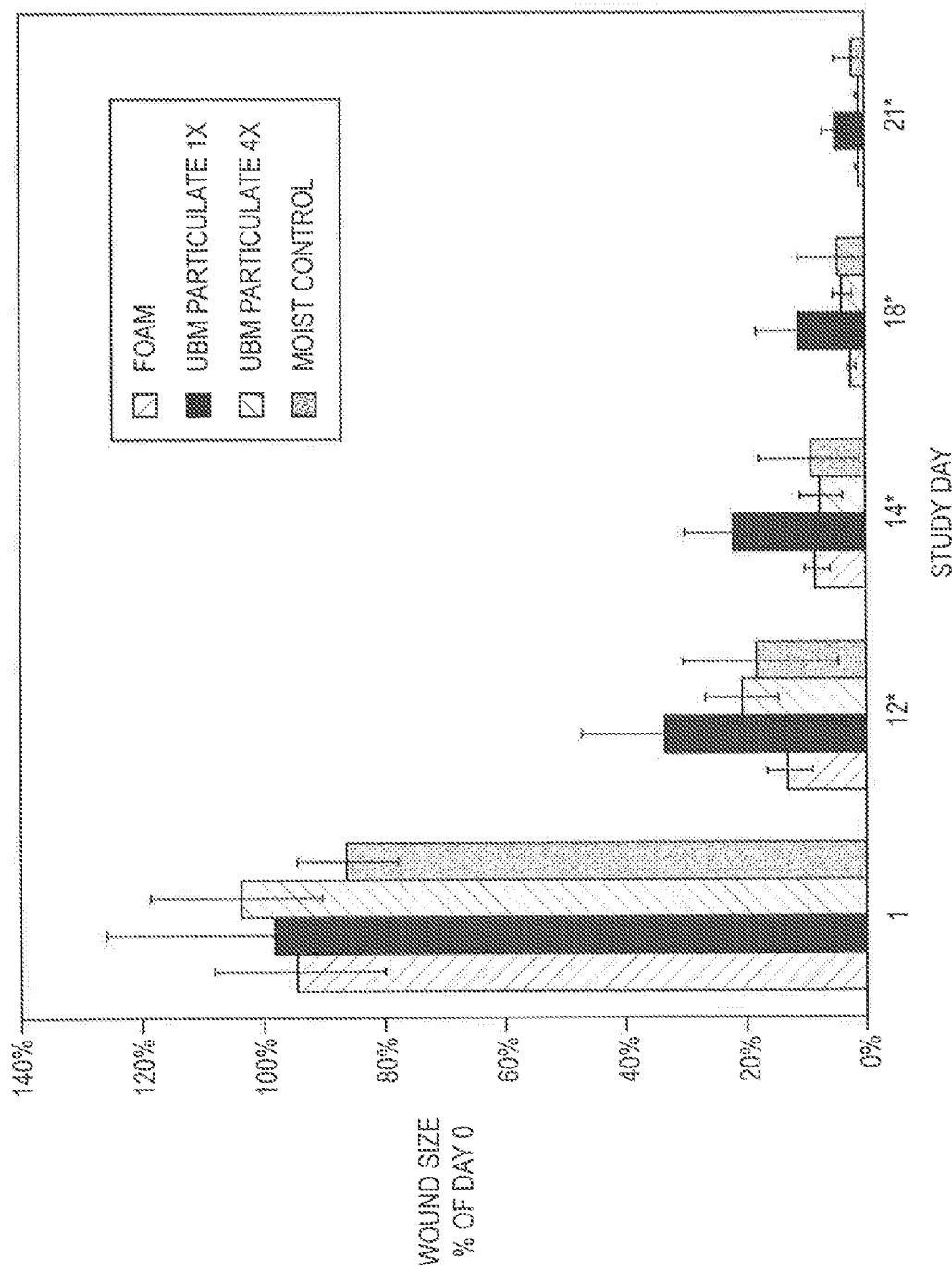
FIG. 4 is a column graph comparing wound healing of the porous ECM foam compared to MicroMatrix 1× (applied once). MicroMatrix 4× (repeated applications of intact UBM particulate on Day 0, Day 4, Day 7, and Day 14), and a moist bandage at various time points after a wound is introduced into the dorsal skin of a pig.

FIG. 4 is a column graph comparing the percentage of the defect diameter that remained at time zero, 1 day, 12 days, 14 days, 18 days, and 21 days for wounds treated with the lyophilized foam discs, 1× (UBM particulate applied one day), 4× (UBM particulate applied on four days), and control.

The full thickness wounds treated with a lyophilized UBM foam disc showed complete healing of the wound defect at 18 days and 21 days grossly and histologically. Histology of the foam disc treated wounds showed that healing was complete by 21 days. Wounds treated with a single application of foam disc showed healing that was marginally faster than multiple applications of the UBM particulate, and significantly faster than a single application of UBM particulate. The treated wound site showed no signs of infection. Vascularization, fat granules and epithelialization at the defect site were observed in the samples implanted with foams.

What is claimed is:

1. A method for making a medical foam device, comprising:
   (a) solubilizing dehydrated extracellular matrix material obtained from a mammalian tissue in a solution comprising a pH less than 4.0 or a pH greater than 9.0;
   (b) foaming said acidified (pH<4) or basic (pH>9) solubilized extracellular matrix material in an industrial blender at speeds in the range of about 500 RPM to 2500 RPM to form a foamy extracellular matrix material;
   (c) neutralizing said foamy extracellular matrix material in a solution to about pH 7; and
   (d) mixing said foamy extracellular matrix material in the solution in step (c) to aid in neutralization of said foaming extracellular matrix material to a pH of about 7;
   (e) introducing said foamy extracellular matrix material of step (d) into a mold;
   (f) lyophilizing said neutralized molded foamy extracellular matrix material by pre-cooled lyophilizer shelves at a temperature range between 25° C. to −40° C.; followed by
   (g) stabilizing said material in step (f) by introducing ice crystals into said molded extracellular matrix material of step (f) at a temperature range between 0° C. to −40° C. at a rate of 0.01° C./min. to 1° C./min. change in temperature for periods of time ranging between 0 minutes to 240 minutes; followed by
   (h) sublimating said ice crystals introduced in step (g) at a vacuum pressure in the range of 100-120 mmHg to produce a porous extracellular matrix medical foam device;
   wherein said porous extracellular matrix material medical foam device comprises a plurality of pores in the interior of the device and a plurality of pores on the exterior of the device, the diameter of the plurality of pores in the interior of the device being different than the diameter of the pores on the exterior of the device.

2. The method of claim 1 wherein said extracellular matrix material is selected from the group consisting of submucosa, epithelial basement membrane, epithelial basement membrane and tunica propria, dermis, and liver basement membrane.

3. The method of claim 1 further comprising particularizing the molded foamy extracellular matrix material after step (h).

4. The method of claim 1 wherein said neutralizing solution is an acid selected from the group consisting of HCl, phosphoric acid, and acetic acid, or a base selected from the group consisting of sodium hydroxide and ammonium hydroxide.

5. The method of claim 1 wherein said neutralizing solution comprises a base selected from the group consisting of NaOH, NaHCO$_3$ and KCl or an acid selected from the group consisting of acetic acid and hydrochloric acid.

6. The method of claim 1 wherein said mold comprises a sheet-like shape.

7. A method for making a medical gel comprising:
   providing the molded foamy extracellular matrix material of claim 1;
   milling said molded foamy extracellular matrix material to form a powder; and
   mixing said powder with an aqueous solution to form said medical gel.

8. The method of claim 1 wherein said plurality of pores in the interior of the porous extracellular matrix material medical foam device has a diameter in the range of about 1 micron to about 500 microns.

* * * * *